(12) United States Patent
MacLeod

(10) Patent No.: US 7,387,623 B2
(45) Date of Patent: Jun. 17, 2008

(54) INJECTABLE PHARMACEUTICAL SUSPENSION IN A TWO-CHAMBER VIAL

(75) Inventor: Steven K. MacLeod, Portage, MI (US)

(73) Assignee: Pfizer Inc., New York, NY (US)

( * ) Notice: Subject to any disclaimer, the term of this patent is extended or adjusted under 35 U.S.C. 154(b) by 582 days.

(21) Appl. No.: 10/644,516

(22) Filed: Aug. 20, 2003

(65) Prior Publication Data

US 2004/0039366 A1 Feb. 26, 2004

Related U.S. Application Data

(60) Provisional application No. 60/404,988, filed on Aug. 21, 2002.

(51) Int. Cl.
*A61B 19/00* (2006.01)
*B65D 81/32* (2006.01)

(52) U.S. Cl. .............................. 604/416; 215/6; 206/219

(58) Field of Classification Search ................ 604/403, 604/410, 415, 416, 89, 90; 128/200.21, 203.12, 128/203.15, 203.21; 220/62.22, 501; 215/6, 215/301, 320, DIG. 3; 206/363–366

See application file for complete search history.

(56) References Cited

U.S. PATENT DOCUMENTS

| | | | | |
|---|---|---|---|---|
| 3,087,638 A | * | 4/1963 | Loper | 206/221 |
| 3,457,348 A | | 7/1969 | Nash et al. | 424/229 |
| 3,464,414 A | | 9/1969 | Sponnoble | 128/272 |
| 4,089,432 A | * | 5/1978 | Crankshaw et al. | 215/6 |
| 4,258,845 A | | 3/1981 | Potts | 206/221 |
| 4,614,267 A | | 9/1986 | Larkin | 206/221 |
| 4,871,354 A | | 10/1989 | Conn et al. | 604/89 |
| 5,335,773 A | | 8/1994 | Haber et al. | 206/221 |
| 5,336,180 A | | 8/1994 | Kriesel et al. | 604/82 |
| 5,350,372 A | | 9/1994 | Ikeda et al. | 604/414 |

(Continued)

FOREIGN PATENT DOCUMENTS

JP 2004337318 A * 12/2004

(Continued)

OTHER PUBLICATIONS

Donbrow et al., (1978), *Journal of Pharmaceutical Sciences*, 67(12), pp. 1676-1681.

(Continued)

*Primary Examiner*—Leslie R Deak
(74) *Attorney, Agent, or Firm*—Gregg C. Benson; Robert M. Kennedy

(57) ABSTRACT

An article of manufacture is provided comprising a vial having (a) a first chamber that is substantially filled with an injectable pharmaceutical formulation; (b) a second chamber that is substantially empty but for a gaseous medium; (c) a septum, impermeable to the gaseous medium, separating the first and second chambers; and (d) actuating means effective to bring the formulation and the gaseous medium into contact by breach of the septum such that the gaseous medium acts as an effective headspace for agitation of the formulation. The formulation comprises an aqueous medium, a drug in solid particulate form in a therapeutically effective amount suspended in the medium, and one or more wetting and/or suspending agents in an amount effective to provide controlled flocculation of the drug, at least one ingredient of the formulation being susceptible to oxidative degradation.

22 Claims, 1 Drawing Sheet

U.S. PATENT DOCUMENTS

| | | | | |
|---|---|---|---|---|
| 5,385,546 A | | 1/1995 | Kriesel et al. | 604/85 |
| 5,549,561 A | * | 8/1996 | Hjertman | 604/131 |
| 6,481,435 B2 | * | 11/2002 | Hochrainer et al. | 128/200.14 |

FOREIGN PATENT DOCUMENTS

| WO | WO 01/87262 | 11/2001 |
|---|---|---|
| WO | WO 01/87266 | 11/2001 |

OTHER PUBLICATIONS

Physicians' Desk Reference, 56th ed. (2002), pp. 2798-2801.
USP 24, NF 19, *U.S. Pharmacopeia*, pp. 2254-2298.
USP 24, NF 19, *U.S. Pharmacopeia*, pp. 2299-2304.

* cited by examiner

INJECTABLE PHARMACEUTICAL SUSPENSION IN A TWO-CHAMBER VIAL

This application claims priority of U.S. provisional application Ser. No. 60/404,988 filed on Aug. 21, 2002.

FIELD OF THE INVENTION

The present invention relates to an article of manufacture and use thereof in delivering to a subject in need thereof a pharmaceutical composition in the form of a ready-to-use aqueous suspension, more particularly such a suspension suitable for parenteral administration, for example by intramuscular, subcutaneous or intradermal injection. The invention relates especially to such an article and use thereof wherein the suspension contains an ingredient that is susceptible to oxidative degradation.

BACKGROUND OF THE INVENTION

A well-known approach to stabilizing an aqueous suspension formulation of a drug, particularly a poorly soluble drug, is by the principle of controlled flocculation. According to such an approach, an aqueous medium or vehicle for the drug is provided that permits aggregation of particles of the drug to form a floc. A desirable floc is one that tends to settle but is readily resuspended with slight agitation and remains in uniform suspension during a period of time long enough to permit administration, for example parenterally, to a subject. Controlled flocculation of a poorly soluble drug generally requires presence in the aqueous medium of one or more wetting agents and one or more suspending agents.

U.S. Pat. No. 3,457,348 to Nash & Haeger, incorporated herein by reference, discloses that polyoxyethylene nonionic surfactants, for example polyoxyethylene sorbitan monooleate, are suitable wetting agents for this purpose. A formulation of sulfadiazine comprising polyoxyethylene sorbitan monooleate and polyethylene glycol (PEG) of molecular weight 4000 is specifically described therein.

Polysorbates such as polysorbate 80 (polyoxyethylene (20) sorbitan monooleate) and PEGs of molecular weight from about 1000 to about 20,000 such as PEG 3350 are known wetting and suspending agents for use in injectable aqueous injection formulations. For example, Depo-Provera® contraceptive injection of Pharmacia & Upjohn is an aqueous suspension formulation of the steroidal drug medroxyprogesterone acetate containing:

| | |
|---|---|
| medroxyprogesterone acetate | 150 mg |
| PEG 3350 | 28.9 mg |
| polysorbate 80 | 2.41 mg |
| sodium chloride | 8.68 mg |
| methylparaben | 1.37 mg |
| propylparaben | 0.15 mg |
| water for injection | q.s. to 1 ml |

See *Physicians' Desk Reference*, 56th ed. (2002), pp. 2798-2801.

It has been found that where an aqueous suspension of a hydrophobic drug includes, for provision of stability through controlled flocculation, compounds such as polysorbates and/or PEGs having polyoxyethylene chains, the suspension tends to show a decline in such stability with time. This decline in stability can be manifested, for example, in thickening of the formulation and/or poor resuspendability of a solid deposit, and, especially in unbuffered or weakly buffered formulations, can be accompanied or mediated by a drift in pH with time, usually a downward drift. Excessive drift in pH of an injectable formulation is undesirable not only for its impact on physical stability of the formulation but also because of the risk of carrying the formulation outside a biocompatible pH range.

Polyoxyethylene chains are susceptible, in presence of oxygen over time, to oxidation of C—H groups to C—O—O—H (hydroperoxy) groups. This oxidative degradation process is known to occur, for example, in polysorbates. See Donbrow et al. (1978), *J. Pharm. Sci.* 67, 1676-1681. The hydroperoxy groups are susceptible to further degradation by a variety of mechanisms, leading to cleavage of the polyoxyethylene chains and, at least in some situations, formation of formic acid and/or other compounds as degradation products with a concomitant lowering of pH. Presence and quantitation of degradation products and/or measurement of pH can provide an indication of the degree of oxidative degradation, if any, that has occurred in a sample of a formulation.

Oxidative degradation can also affect formulation ingredients other than those comprising polyoxyethylene chains, with a variety of undesirable effects, including, in addition to decline in physical stability and pH drift, accumulation of degradation products that can be toxic or otherwise deleterious if administered by injection, and, where the ingredient subject to oxidative degradation is an active ingredient, loss of potency.

By reducing or minimizing exposure of the formulation to oxygen, problems of oxidative degradation can be substantially overcome. For example, if an injectable formulation is packaged in an airtight container such as a vial having little or no headspace acting as a reservoir of gaseous oxygen, i.e., if the container is substantially filled with the formulation, oxidative degradation is likely to be minimized. This can be an acceptable way to package a formulation that does not require agitation to homogenize the formulation prior to use, for example a formulation in the form of an aqueous solution. However, the lack of headspace becomes a serious problem in the case of an aqueous suspension formulation exhibiting controlled flocculation, because it greatly impedes ability to agitate the formulation, for example by shaking the container, to resuspend a settled floc and provide a fine homogeneous suspension for parenteral injection. Where the formulation is packaged in a unit-dose container such as a vial, it is particularly important to be able to resuspend substantially all of a drug deposit so that the full dose can be administered.

One approach to reducing exposure of an aqueous suspension formulation to oxygen yet providing a sufficient headspace for agitation is to provide an oxygen-depleted atmosphere in the headspace, for example an atmosphere enriched in nitrogen or a noble gas. This approach is not always convenient, and it can be difficult and expensive in practice to displace substantially all of the oxygen from headspace atmosphere.

It would be of benefit in the art to provide an alternative means of reducing exposure to oxygen of an injectable aqueous suspension formulation, that permits resuspension by agitation immediately prior to use.

SUMMARY OF THE INVENTION

There is now provided an article of manufacture comprising a vial having at least two chambers. A first chamber of the vial is substantially filled with a parenterally deliverable formulation that comprises (i) an aqueous medium, (ii) a drug in solid particulate form in a therapeutically effective amount suspended in the medium, and (iii) one or more wetting and/or suspending agents in an amount effective to provide controlled flocculation of the drug, at least one ingredient of the formulation being susceptible to oxidative degradation. A second chamber of the vial is substantially empty but for a gaseous medium, and is separated from the first chamber by a septum that is substantially impermeable to the gaseous medium. The vial further comprises actuating means effective to bring the formulation and the gaseous medium into contact by breach of the septum such that the gaseous medium acts as an effective headspace for agitation of the formulation.

In a preferred embodiment the at least one ingredient of the formulation that is susceptible to oxidative degradation (herein such ingredient is referred to as the "susceptible agent") is a wetting and/or suspending agent, for example, such an agent comprising one or more polyoxyethylene chains.

It has surprisingly been found that by protecting the susceptible agent from oxidative degradation, the formulation exhibits significantly improved physical stability during storage, as manifested for example by a significantly reduced tendency of the drug to form deposits that are difficult to resuspend. It has also been observed that significant improvement in pH stability of the formulation can result from such protection.

By "oxidative degradation" is meant chemical change in a susceptible agent arising from reaction with oxygen or other oxidizing agent. It will be understood that the present invention applies to an article as defined above whether or not the drug itself is susceptible to oxidative degradation; in a particular embodiment, however, the drug is one that exhibits substantial chemical stability in presence of oxygen.

Many wetting and/or suspending agents useful in preparing parenterally deliverable suspensions have been found to be susceptible to oxidative degradation in an aqueous medium. Examples of such agents are those comprising polyoxyethylene chains, for example polyethylene glycols and polyoxyethylene surfactants such as polysorbates. In presence of oxygen, the wetting and/or suspending properties of these agents are gradually lost as degradation occurs. It is believed, without being bound by theory, that this loss of wetting and/or suspending properties due to oxidative degradation causes, or at least contributes substantially to, physical instability of a suspension composition lacking means for restricting exposure to oxygen. Practice of the present invention typically results in significantly reduced oxidative degradation of one or more wetting and/or suspending agents and thereby, it is believed, significantly enhanced physical stability as illustrated herein.

In a particularly preferred embodiment of the invention, the susceptible agent is a polysorbate surfactant, for example polysorbate 80. The invention is illustrated herein with particular reference to an article containing a formulation wherein the drug is medroxyprogesterone acetate.

There is further provided a method of use of an article as described above in preparing a filled syringe for parenteral injection of a drug into a subject. The method comprises a step of actuating the vial to bring the formulation and the gaseous medium into contact by breach of the septum; a step of agitating the vial to permit the formulation and the gaseous medium to interact to resuspend settled particulate material in the formulation to form a substantially homogeneous suspension; and a step of withdrawing the suspension into a syringe.

DETAILED DESCRIPTION OF THE INVENTION

As indicated above, the present invention provides an article of manufacture comprising a vial having (a) a first chamber that is substantially filled with an aqueous suspension formulation as described herein having properties of controlled flocculation; (b) a second chamber that is substantially empty but for a gaseous medium; (c) a septum, impermeable to the gaseous medium, separating the first and second chambers; and (d) actuating means effective to bring the formulation and the gaseous medium into contact by breach of the septum such that the gaseous medium acts as an effective headspace for agitation of the formulation.

The formulation in the vial as transported and stored prior to use is not in contact with a significant headspace volume, thus exposure of the formulation to oxygen is minimized and the susceptible agent in the formulation is thereby protected from oxidative degradation. However, immediately prior to use, the vial can be actuated to create a headspace permitting ready agitation for resuspension of the formulation. There is generally no need for the gaseous medium that becomes the headspace to be oxygen-depleted, as the formulation is in contact with the headspace for only a short period of time. A preferred gaseous medium according to this embodiment is air, but an oxygen-depleted atmosphere, for example one enriched in nitrogen and/or a noble gas, can, if desired, be used.

Figure 1:
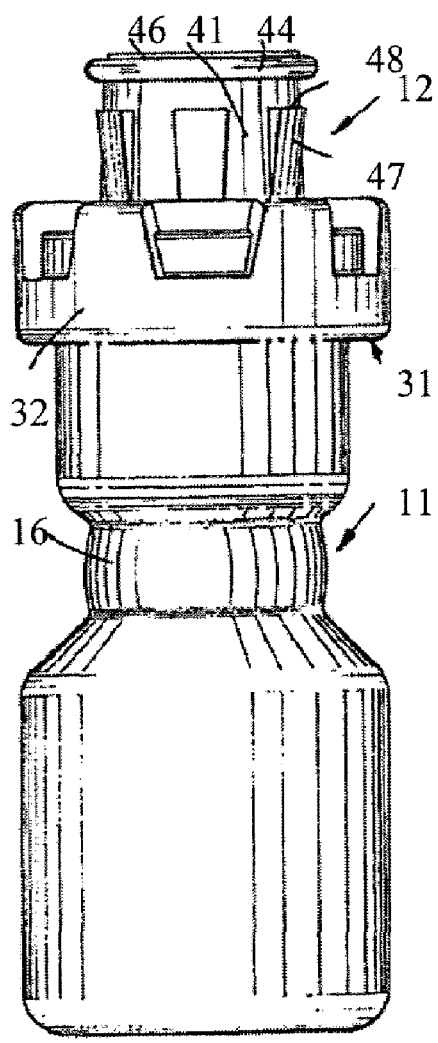
FIG. 1 is a side elevation of a two-compartment mixing vial that is an illustrative embodiment of the invention.
Figure 2:
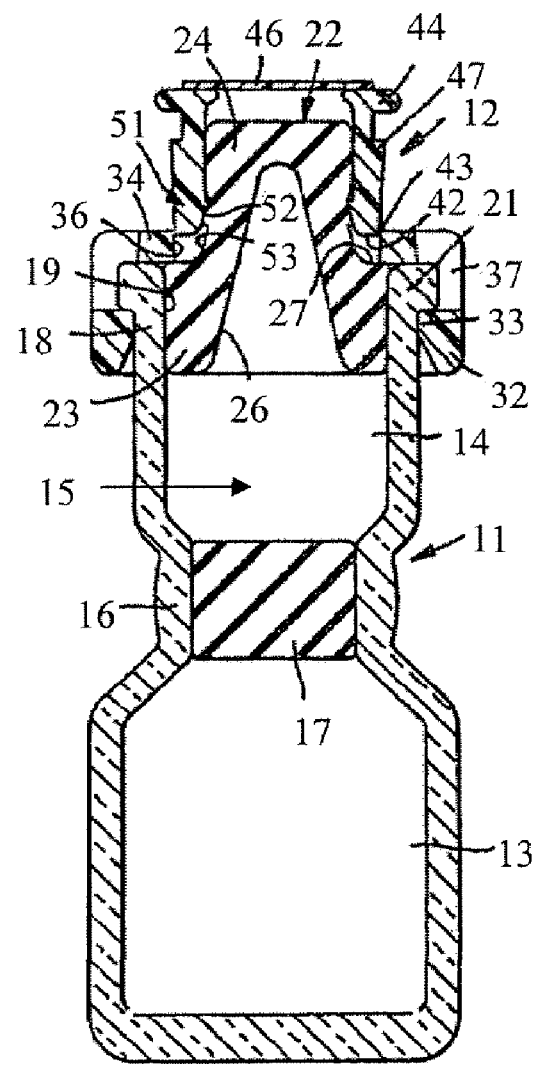
FIG. 2 is a central sectional view of the vial shown in FIG. 1.

An illustrative two-compartment mixing vial suitable for the present purpose is disclosed in U.S. Pat. No. 4,258,845 to Potts, incorporated herein by reference, and is shown in FIGS. 1 and 2 herein. Specific details of this illustrative vial that are not explicitly described hereinbelow are available to the reader by reference to above-cited U.S. Pat. No. 4,258,845.

The illustrative vial 11, constructed of any suitable material, preferably glass, defines therein two interior compartments, a lower compartment 13 and an upper compartment 14 which are separated by a constriction 16 in which a substantially airtight and watertight plug 17 is engaged. The plug can be made of any suitable material, but is preferably of butyl rubber coated with at silicone fluid to maintain an effective seal as described in U.S. Pat. No. 3,464,414 to Sponnoble, incorporated herein by references. The upper compartment 14 corresponds to the "first chamber" and the lower compartment 13 to the "second chamber" as defined above. The upper compartment 14 is substantially filled with the aqueous suspension formulation 15 as described herein. The plug 17 corresponds to the septum separating the two chambers as defined above.

The vial 11 has an annular neck 18 at one end thereof, defining an opening 19 for communication between a free end of the neck 18 and the interior of the upper compartment 14. The neck 18 in the illustrated embodiment is of substantially the same interior diameter as the upper compartment 14, but optionally the neck 18 can be of reduced diameter. Typically the neck 18, adjacent the free end thereof, has a radially outward projecting annular rim 21. The upper compartment 14 is substantially filled with an aqueous suspension formulation as described herein, and the lower compartment 13 contains only a gaseous medium, for example air.

The neck 18 is provided with a closure structure 12 that can be of any suitable design, but in the illustrated embodiment comprises a resiliently flexible stopper 22 that is preferably fabricated from an elastomer that is impervious to water and air, for example butyl rubber. The stopper 22 has a lower sealing portion 23 seated within the neck 18 of the vial. To improve the seal formed between the sealing portion 23 of the stopper and the neck 18 of the vial, the periphery of the sealing portion 23 can, if desired, be provided with one to a plurality of spaced annular ridges. The stopper 22 also has an upper protruding portion 24 that projects coaxially beyond the free end of the neck 18 of the vial. The stopper 22 preferably has a deep recess 26, typically having the shape of a cone having a blunted or truncated apex. The base of the recess 26 opens into the upper compartment 14 and the apex of the recess 26 is in proximity to the upper surface of the protruding portion 24. A thin wall portion of the stopper 22 between the upper surface of the protruding portion 24 and the apex of the recess 26 permits a sharp tip of a syringe needle to be inserted through the thin wall into the upper compartment 14 for withdrawal of the formulation therein. The protruding portion 24 is smaller in diameter than the sealing portion 23 and at the interface therewith defines an upwardly facing annular shoulder 27, which, prior to actuation of the vial as described below, is substantially flush with the upper surface of the annular rim 21 of the neck portion of the vial.

The closure structure 12 further comprises a cap assembly 31 that incorporates an actuating means, preferably a means for applying hydraulic pressure via the stopper 22 to the liquid formulation in the upper compartment 14. Such pressure is transmissible by the liquid formulation to the plug 17 and tends to disengage the plug from the constriction 18 of the vial, pushing the plug into the lower compartment 13, thereby bringing the formulation in the upper compartment 14 into contact with the gaseous medium in the lower compartment 13. The cap assembly is typically formed from a somewhat rigid material, typically a plastic such as polyethylene or polypropylene.

In the illustrated embodiment the means for applying hydraulic pressure comprises a sleeve 41 of the cap assembly, which is snugly disposed around and slidingly engaged with the protruding portion 24 of the stopper. The sleeve 41 has at its upper end a radially outward directed annular flange 44 and at its lower end an annular face 42 that, prior to actuation of the vial, is spaced upwardly a substantial distance from the shoulder 27 of the stopper. Adjacent to the lower end face 42, the sleeve 41 is connected to an annular gripping portion 32 by a fracturable connection 43, which can be formed as a thin annular flange or a plurality of spaced webs. The open upper end of the sleeve 41 is preferably covered by a manually removable seal 46 formed of a suitable material such as metallic foil.

The gripping portion 32 surrounds the rim 21 and has at its lower edge a plurality of substantially uniformly spaced projections 33 extending radially inward. The inner surfaces of the projections 33 define a circle having a diameter somewhat less than the outside diameter of the rim 21, such that the projections 33 resiliently snap into position directly under the rim 21 to effect a secure locking of the cap assembly on to the neck of the vial. The gripping portion 32 comprises an annular plate 34 that overlies the upper end of the neck 18 of the vial. The annular plate 34 circumscribes a plate opening 36 of diameter smaller than the neck opening 19, such that the annular plate 34 projects radially inward to overlap the shoulder 27 of the stopper, thereby positively retaining the stopper 22 in the neck 18 of the vial. The diameter of the opening 36 is also smaller than the outer diameter of the flange 44. The gripping portion 32 can, as illustrated, have a plurality of circumferentially spaced openings 37 to help provide resiliency to the gripping portion 32 for snap-fitting on to the vial.

The outer surface of the sleeve 41 is, in the illustrated embodiment, provided with a plurality of parallel and substantially uniformly spaced ramps 47 that extend axially from and converge with the sleeve 41 toward the gripping portion 32. The diameter of the circle described by the lower ends of the ramps 47 is approximately equal to that of the opening 36, but the upper ends 48 of the ramps describe a circle having a somewhat greater diameter than that of the opening 36. The ramps 47 function as a locking means for retaining the sleeve 41 in its actuated position as described below.

The cap assembly as illustrated has a lock structure 51 that coacts with the stopper 22 to prevent the stopper from being slidably displaced downward relative to the sleeve 41. Typically the lock structure 51 comprises a lock ring 52 projecting inward from the lower end of the sleeve 41. In cross-section, the lock ring 52 has a toothlike configuration such that the inner surface thereof tapers inwardly as it projects upwardly, and terminates in an upwardly facing shoulder. The lock ring 52 is thereby effective in only one direction and enables the sleeve 41 to be slidably displaced downward relative to the stopper 22. Typically the lock structure 51 further comprises an undercut annular groove 53 formed in the stopper 22 directly above the shoulder 27 thereof. The groove 53 terminates in a downwardly facing shoulder at its upper edge.

To actuate the vial, the sleeve 41 is pressed downward, for example with a thumb, thereby breaking the fracturable connection 43 and moving the lower end face 42 of the sleeve toward the shoulder 27 of the stopper until the lock ring 52 engages with the groove 53. Continued depression of the sleeve 41 pushes the stopper 22 downward, creating hydraulic pressure in the upper compartment 14. Depression of the sleeve 41 can continue only until the flange 44 abuts the annular plate 34, thereby preventing the stopper 22 from being pushed too far into the upper compartment 14. When the sleeve 41 is fully depressed, the ramps 47 fixedly lock the closure structure 12 in the actuated state and prevent re-use of the vial, as the closure structure cannot be disassembled from the vial without destruction or permanent damage to the closure structure.

A mixing vial as described above is in commercial use, for example as a packaging system for Solu-Corte® hydrocortisone sodium succinate for injection, under the name Act-O-Vial® of Pharmacia Corporation. However, such a vial has previously been described for use only with a lyophilized powder formulation of a drug in the lower compartment and an aqueous diluent in the upper compartment. According to the present embodiment, the mixing vial now contemplated differs from that known in the art at least by having an aqueous suspension formulation in the upper compartment and only a gaseous medium, typically air, in the lower compartment. The lower compartment as presently contemplated functions as a reservoir for air or other gaseous medium to provide a headspace for effective agitation following actuation of the vial, but, by virtue of its lack of contact with the upper compartment prior to actuation, minimizes or prevents exposure to oxygen of ingredients of the formulation that are susceptible to oxidative degradation.

Accordingly, in a particular embodiment, an article of manufacture of the present invention comprises an Act-O-Vial® or substantially similar mixing vial containing, in an upper compartment thereof, a formulation that comprises (a) an aqueous medium having dispersed therein, in solid particulate form, a steroidal drug in a therapeutically effective amount and (b) one or more wetting and/or suspending agents in an amount effective to provide controlled flocculation of the drug, at least one of the wetting and/or suspending agents being susceptible to oxidative degradation; and, in a lower compartment thereof, only a gaseous medium, for example air.

It will be apparent to those of skill in the art that many modifications can be made to the article of manufacture described immediately above without taking the article outside the scope of the present invention. For example, the actuating means can comprise, in place of a means for applying hydraulic pressure to the contents of the upper compartment, a substantially rigid member that, when a downward force is applied to the cap assembly or a portion thereof, transmits the force directly to the septum or plug separating the upper and lower compartments.

Other two-chamber devices that can be substituted include those described, for example, in the patents individually listed below, each incorporated herein by reference.

Above-cited U.S. Pat. No. 3,464,414.
U.S. Pat. No. 4,614,267 to Larkin.
U.S. Pat. No. 4,871,354 to Conn et al.
U.S. Pat. No. 5,335,773 to Haber et al.
U.S. Pat. No. 5,336,180 to Kriesel & Thompson.
U.S. Pat. No. 5,350,372 to Ikeda et al.
U.S. Pat. No. 5,385,546 to Kriesel & Thompson.

Other than the Act-O-Vial® system of Pharmacia Corporation, two-chamber systems in commercial use for mixing a lyophilized powder with a diluent include those sold under the names Univial™ and ADD-Vantage™ of Abbott Laboratories and Piggyback™ of SmithKline Beecham.

An article of the invention comprises, in the formulation that substantially fills the first chamber of the vial, a drug in a therapeutically effective amount. Typically the drug is one of low solubility in water, for example having a solubility of less than about 10 mg/ml, illustratively less than about 1 mg/ml or even less than about 0.1 mg/ml.

Solubility in water for many pharmaceutically useful compounds can be readily determined from standard pharmaceutical reference books, for example *The Merck Index,* 13th ed., 2001 (published by Merck & Co., Inc., Rahway, N.J.); the *United States Pharmacopeia,* 24th ed. (USP 24), 2000; *The Extra Pharmacopoeia,* 29th ed., 1989 (published by Pharmaceutical Press, London); and the *Physicians Desk Reference* (PDR), 2001 ed. (published by Medical Economics Co., Montvale, N.J.).

For example, individual compounds of low solubility include compounds categorized as "slightly soluble", "very slightly soluble", "practically insoluble" and "insoluble" in USP 24, pp. 2254-2298; and compounds categorized as requiring 100 ml or more of water to dissolve 1 g of the drug, as listed in USP 24, pp. 2299-2304.

Illustratively, suitable drugs of low water solubility include, without limitation, drugs from the following classes: abortifacients, ACE inhibitors, α- and β-adrenergic agonists, α- and β-adrenergic blockers, adrenocortical suppressants, adrenocorticotropic hormones, alcohol deterrents, aldose reductase inhibitors, aldosterone antagonists, anabolics, analgesics (including narcotic and non-narcotic analgesics), androgens, angiotensin II receptor antagonists, anorexics, antacids, anthelninthics, antiacne agents, antiallergics, antialopecia agents, antiamebics, antiandrogens, antianginal agents, antiarrhythmics, antiarteriosclerotics, antiarthritic/antirheumatic agents (including selective COX-2 inhibitors), antiasthmatics, antibacterials, antibacterial adjuncts, anticholinergics, anticoagulants, anticonvulsants, antidepressants, antidiabetics, antidiarrheal agents, antidiuretics, antidotes to poison, antidyskinetics, antieczematics, antiemetics, antiestrogens, antifibrotics, antiflatulents, antifungals, antiglaucoma agents, antigonadotropins, antigout agents, antihistaminics, antihyperactives, antihyperlipoproteinemics, antihyperphosphatemics, antihypertensives, antihyperthyroid agents, antihypotensives, antihypothyroid agents, antiinflammatories, antimalarials, antimanics, antimethemoglobinemics, antimigraine agents, antimuscarinics, antimycobacterials, antineoplastic agents and adjuncts, antineutropenics, antiosteoporotics, antipagetics, antiparkinsonian agents, antipheochromocytoma agents, antipneumocystis agents, antiprostatic hypertrophy agents, antiprotozoals, antipruritics, antipsoriatics, antipsychotics, antipyretics, antirickettsials, antiseborrheics, antiseptics/disinfectants, antispasmodics, antisyphylitics, antithrombocythemics, antithrombotics, antitussives, antiulceratives, antiurolithics, antivenins, antiviral agents, anxiolytics, aromatase inhibitors, astringents, benzodiazepine antagonists, bone resorption inhibitors, bradycardic agents, bradykinin antagonists, bronchodilators, calcium channel blockers, calcium regulators, carbonic anhydrase inhibitors, cardiotonics, CCK antagonists, chelating agents, cholelitholytic agents, choleretics, cholinergics, cholinesterase inhibitors, cholinesterase reactivators, CNS stimulants, contraceptives, debriding agents, decongestants, depigmentors, dermatitis herpetiformis suppressants, digestive aids, diuretics, dopamine receptor agonists, dopamine receptor antagonists, ectoparasiticides, emetics, enkephalinase inhibitors, enzymes, enzyme cofactors, estrogens, expectorants, fibrinogen receptor antagonists, fluoride supplements, gastric and pancreatic secretion stimulants, gastric cytoprotectants, gastric proton pump inhibitors, gastric secretion inhibitors, gastroprokinetics, glucocorticoids, α-glucosidase inhibitors, gonad-stimulating principles, growth hormone inhibitors, growth hormone releasing factors, growth stimulants, hematinics, hematopoietics, hemolytics, hemostatics, heparin antagonists, hepatic enzyme inducers, hepatoprotectants, histamine $H_2$ receptor antagonists, HIV protease inhibitors, HMG CoA reductase inhibitors, immunomodulators, immunosuppressants, insulin sensitizers, ion exchange resins, keratolytics, lactation stimulating hormones, laxatives/cathartics, leukotriene antagonists, LH-RH agonists, lipotropics, 5-lipoxygenase inhibitors, lupus erythematosus suppressants, matrix metalloproteinase inhibitors, mineralocorticoids, miotics, monoamine oxidase inhibitors, mucolytics, muscle relaxants, mydriatics, narcotic antagonists, neuroprotectives, nootropics, ovarian hormones, oxytocics, pepsin inhibitors, pigmentation agents, plasma volume expanders, potassium channel activators/openers, progestogens, prolactin inhibitors, prostaglandins, protease inhibitors, radio-pharmaceuticals, 5α-reductase inhibitors, respiratory stimulants, reverse transcriptase inhibitors, sedatives/hypnotics, serenics, serotonin noradrenaline reuptake inhibitors, serotonin receptor agonists, serotonin receptor antagonists, serotonin uptake inhibitors, somatostatin analogs, thrombolytics, thromboxane $A_2$ receptor antagonists, thyroid hormones, thyrotropic hormones, tocolytics, topoisomerase I and II inhibitors, uricosurics, vasomodulators including vasodilators and vasoconstrictors, vasoprotectants, xanthine oxidase inhibitors, and combinations thereof Non-limiting illustrative examples of suitable drugs of low water solubility include acetohexamide, acetylsalicylic acid, alclofenac, allopurinol, atropine, benzthiazide, carprofen, celecoxib, chlordiazepoxide, chlorpromazine, clonidine, codeine, codeine phosphate, codeine sulfate, deracoxib, diacerein, diclofenac, diltiazem, eplerenone, estradiol, etodolac, etoposide, etoricoxib, fenbufen, fenclofenac, fenprofen, fentiazac, flurbiprofen, griseofulvin, haloperidol, ibuprofen, indomethacin, indoprofen, ketoprofen, lorazepam, medroxyprogesterone acetate, megestrol, methoxsalen, methylprednisone, morphine, morphine sulfate, naproxen, nicergoline, nifedipine, niflumic, oxaprozin, oxazepam, oxyphenbutazone, paclitaxel, phenindione, phenobarbital, piroxicam, pirprofen, prednisolone, prednisone, procaine, progesterone, pyrimethamine, rofecoxib, sulfadiazine, sulfamerazine, sulfisoxazole, sulindac, suprofen, temazepam, tiaprofenic acid, tilomisole, tolmetic, valdecoxib, etc.

The amount of drug incorporated in a drug-containing composition of the invention can be selected according to known principles of pharmacy. A therapeutically and/or prophylactically effective amount of drug is specifically contemplated, i.e., an amount of drug that is sufficient to elicit in a subject the required or desired therapeutic and/or prophylactic response when parenterally administered to the subject.

In one embodiment, the drug is a steroid. Steroidal drugs include without limitation those useful as abortifacients, adrenocortical suppressants, aldosterone antagonists, anabolics, androgens, anesthetics, antiallergics, antiandrogens, antiasthmatics, antigonadotropins, antihyperlipoproteinemics, anti-inflammatories, antineoplastics, antiprogestins, antipruritics, antirachitics, aromatase inhibitors, contraceptives, estrogens, glucocorticoids, mineralocorticoids and progestogens. Illustrative examples of such drugs include 21-acetoxypregnenolone, alclometasone, aldosterone, alfadolone, alfaxalone, algestone, allylestrenol, amcinonide, anagestone, androisoxazole, androstane, androstane-3β,11β-diol-17-one, androstenediol, androstenedione, (3α,5α)-androst-16-en-3-ol, androsterone, beclomethasone, betamethasone, bolandiol, bolasterone, boldenone, budesonide, calusterone, canrenone, chlormadinone, chloroprednisone, ciclesonide, clobetasol, clobetasone, clocortolone, clomestrone, cloprednol, clostebol, cloxotestosterone, colpormon, corticosterone, cortisone, cortivazol, cyproterone, danazol, deflazacort, delmadinone, demegestone, deoxycorticosterone, desogestrel, desonide, desoximetasone, dexamethasone, dichlorisone, dienogest, diflorasone, diflucortolone, difluprednate, dimethisterone, dromostanolone, drospirenone, dutasteride, dydrogesterone, epimestrol, epitiostanol, eplerenone, epostane, episteride, equilenin, equilin, ergosterol, estradiol, α-estradiol, estramustine, estriol, estrone, ethinyl estradiol, ethisterone, ethylestrenol, ethynodiol, etonogestrel, exemestane, fluazacort, flucloronide, fludrocortisone, flumethasone, flunisolide, fluocinolone, fluocinonide, fluocortin, fluocortolone, fluorometholone, fluoxymesterone, fluperolone, fluprednidene, fluprednisolone, flurandrenolide, flurogestone, fluticasone, formebolone, formestane, formocortal, gestodene, gestonorone, gestrinone, halcinonide, halobetasol, halometasone, halopredone, hydrocortamate, hydrocortisone, hydroxydione, 17α-hydroxyprogesterone, loteprednol, lynestrenol, mazipredone, medrogestone, medroxyprogesterone, medrysone, megestrol, melengestrol, mepitiostane, meprednisone, mestanolone, mesterolone, mestranol, methandriol, methandrostenolone, methenolone, methylprednisolone, 17-methyltestosterone, methyltrienolone, mifepristone, mometasone, moxestrol, nandrolone, norbolethone, norethandrolone, norethindrone, norethynodrel, norgesterone, norgestimate, norgestrel, norgestrienone, normethandrone, norvinisterone, onapristone, osaterone, oxabolone, oxandrolone, oxendolone, oxymesterone, oxymetholone, paramethasone, pentagestrone, prasterone, prednicarbate, prednimustine, prednisolone, prednisone, prednival, prednylidene, pregnan-3α-ol-20-one, progesterone, promegestone, quinbolone, quinestradiol, quinestrol, rimexolone, spironolactone, stanolone, stanozolol, stenbolone, testosterone, tixocortol, trenbolone, trengestone, triamcinolone, trilostane and pharmaceutically acceptable esters, salts, enantiomers, epimers and tautomers thereof.

Presently preferred steroidal drugs include clostebol, eplerenone, estradiol, exemestane, medroxyprogesterone, methylprednisolone, oxabolone, testosterone and pharmaceutically acceptable esters and salts thereof, for example clostebol acetate, estradiol 17β-cypionate, medroxyprogesterone 17-acetate, methylprednisolone 21-acetate, oxabolone cypionate and testosterone 17β-cypionate. In a particularly preferred embodiment, the steroidal drug is selected from estradiol cypionate, exemestane and medroxyprogesterone acetate. More than one steroidal drug, for example a combination of estradiol cypionate and medroxyprogesterone acetate, can be present.

What constitutes a therapeutically effective amount of the drug in the formulation depends on the drug in question, the indication for which it is to be administered to a subject, the age and body weight of the subject, and other factors. In the case of estradiol cypionate, the drug is typically present in a concentration of about 1 to about 50 mg/ml, preferably about 2.5 to about 25 mg/ml. In the case of medroxyprogesterone acetate, the drug is typically present in a concentration of about 10 to about 400 mg/ml, preferably about 30 to about 300 mg/ml, and more preferably about 50 to about 200 mg/ml, for example about 100 mg/ml or about 150 mg/ml. When both estradiol cypionate and medroxyprogesterone are present, the concentrations of the individual drugs are typically as given above. In the case of exemestane, the drug is typically present in a concentration of about 10 to about 250 mg/ml, preferably about 50 to about 200 mg/ml.

To enhance suspension stability, the drug particles are preferably very small, for example having a weight mean particle size smaller than about 100 μm, typically about 1 to about 100 μm. It is sometimes desirable that the drug be micronized, i.e., reduced to an average particle size of about 1 to about 25 μm. Optionally all or a portion of the drug can be in nanoparticulate form, i.e., having an average particle size smaller than 1 μm (1000 nm), for example about 100 to about 900 nm, more particularly about 500 to about 900 nm.

The formulation comprises one or more wetting and/or suspending agents in an amount effective to provide controlled flocculation of the drug, and in a preferred embodiment at least one of the wetting and/or suspending agents is susceptible to oxidative degradation. In one embodiment, the at least one susceptible wetting and/or suspending agent comprises a polyoxyethylene chain.

It is believed, without being bound by theory, that the sometimes observed gradual loss of controlled flocculation behavior of a composition such as the Depo-Provera® formulation described above is due at least in part, in many cases due primarily, to loss of surfactancy of the wetting and/or suspending agent resulting from oxidative cleavage of polyoxyethylene chains.

Oxidative degradation susceptible wetting and/or suspending agents useful in formulations packaged in articles of the invention include any pharmaceutically acceptable agent that comprises one or more polyoxyethylene chains.

Such agents include polyethylene glycols (PEGs), for example those of average molecular weight from about 100 to about 20,000, more typically about 200 to about 10,000, most typically about 300 to about 6000. Suitable PEGs illustratively include PEG 2000, having an average molecular weight of 1800 to 2200, PEG 3000, having an average molecular weight of 2700 to 3300, PEG 3350, having an average molecular weight of 3000 to 3700, PEG 4000, having an average molecular weight of 3000 to 4800, and PEG 4600, having an average molecular weight of 4400 to 4800. PEG 3350 and PEG 4000 are especially preferred. Such PEGs act as density adjusting agents, thereby enhancing suspension stability.

Such agents further include poloxamers (polyoxyethylene-polyoxypropylene copolymers), illustratively of grades listed in the *United States Pharmacopeia* such as poloxamers 124, 188, 237, 338 and 407.

Such agents further include surfactants having a hydrophobic alkyl or acyl group, typically of about 8 to about 18 carbon atoms, and a hydrophilic polyoxyethylene chain. Preferred such surfactants are nonionic surfactants, illustratively including polyoxyethylene alkyl ethers such as laureth-9, laureth-23, ceteth-10, ceteth-20, oleth-10, oleth-20, steareth-10, steareth-20 and steareth-100; polyoxyethylene castor oil, polyoxyethylene hydrogenated castor oil, polysorbates such as polysorbate 20, polysorbate 40, polysorbate 60, polysorbate 65, polysorbate 80, polysorbate 85 and polysorbate 120; and polyoxyethylene alkyl esters, for example polyoxyethylene stearates. Polysorbates, for example polysorbate 80, are particularly preferred.

According to the present embodiment, the susceptible wetting and/or suspending agent(s), together with any other wetting and/or suspending agents that can optionally be included in the formulation, are present in total and relative amounts providing acceptable controlled flocculation properties as defined above. The smaller the amount of susceptible agent that is used to provide wetting and/or suspending properties consistent with controlled flocculation, the greater is the risk of loss of formulation stability due to oxidative degradation.

In the case of a nonionic polyoxyethylene surfactant such as polysorbate 80, for example, a useful concentration can be as low as about 0.5 to about 10 mg/ml, typically about 1 to about 5 mg/ml.

In the case of a PEG such as PEG 3350, a useful concentration is illustratively about 5 to about 100 mg/ml, typically about 10 to about 50 mg/ml.

The formulation optionally further comprises an antioxidant or oxygen scavenger. Non-limiting illustrative examples of suitable antioxidants include tocopherols such as α-tocopherol (vitamin E), ascorbic acid (vitamin C) and salts and esters thereof including sodium ascorbate and ascorbic acid palmitate, isoascorbic acid (erythorbic acid), butylated hydroxyanisole (BHA), butylated hydroxytoluene (BHT), thiol derivatives including acetylcysteine, cysteine, cystine, dithioerythritol, dithiothreitol, glutathione, methionine and thioglycerol, especially L-methionine, fumaric acid and salts thereof, hypophosphorous acid, malic acid, 6-hydroxy-2,5,7,8-tetramethylchroman-2-carboxylic acid (Trolox™), alkyl gallates, for example propyl gallate, octyl gallate and lauryl gallate, nordihydroguaiaretic acid, and sodium and potassium thiosulfate, sulfite, bisulfite and metabisulfite. An especially preferred antioxidant is L-methionine. As shown in International Patent Application No. WO 01/87266, L-methionine has a pH stabilizing effect on an aqueous suspension formulation of a steroidal drug that cannot be fully explained merely by its antioxidant effect.

One or more free radical-scavenging antioxidants are optionally present in a total amount effective to substantially reduce oxidative degradation of a susceptible agent, typically in a total concentration of about 0.1 to about 50 mg/ml, preferably about 0.2 to about 20 mg/ml, and more preferably about 0.5 to about 10 mg/ml. Illustratively, L-methionine can usefully be present at a concentration of about 1 to about 5 mg/ml.

It is believed, without being bound by theory, that antioxidants reduce oxidative degradation by inhibiting accumulation of hydroperoxides and/or free radicals, an initial step in the oxidative degradation process. Such hydroperoxides and free radicals can accelerate the degradation process in a form of autoxidation, as described for example by Donbrow et al., op. cit. By scavenging hydroperoxides and free radicals, antioxidants can significantly slow down the oxidative degradation of PEGs, polyoxyethylene surfactants and other susceptible ingredients of a composition.

The formulation optionally further comprises a chelating agent. Again it is believed, without being bound by theory, that chelating agents inhibit hydroperoxide formation and thereby slow down oxidative degradation. Trace metal ion contaminants, particularly transition elements such as iron, are believed, under certain conditions, to accelerate oxidation and by sequestering such contaminants a chelating agent can provide some degree of protection from oxidation of an oxidative degradation susceptible ingredient.

Further degradation of hydroperoxides is believed to be accelerated in acid conditions; it is thus be beneficial to use a chelating agent that is capable of sequestering metal ions in media having a pH that is not strongly acidic, particularly such a chelating agent with some buffering capacity. An illustrative example is diethylenetriaminepentaacetic acid (DTPA) and pharmaceutically acceptable salts thereof, e.g., the pentasodium salt. Other suitable compounds of a similar nature include ethylenediaminetetraacetic acid (EDTA), nitrilotriacetic acid (NTA), ethylenediamine-bis(o-hydroxyphenylacetic acid) (EDDA), bis(aminoethyl)glycolether-N, N,N',N'-tetraacetic acid (EGTA) and pharmaceutically acceptable salts thereof. Other classes of compound that can be useful as chelating agents include polyfunctional acids such as citric acid and oxalic acid, amines such as porphyrins, phenanthrolines, triethanolamine, tromethamine and dimethylglyoxime, and sulfur-containing compounds such as 2,3-dimercaptopropanol. Chelating agents can illustratively be included at concentrations of about 0.1 to about 20 mg/ml, preferably about 0.2 to about 10 mg/ml, and more preferably about 0.5 to about 5 mg/ml.

Optionally, the formulation can comprise, in addition to components described hereinabove, excipients such as those mentioned below.

One or more additional wetting and/or suspending agents, not susceptible to oxidative degradation as described above, can optionally be present. Such agents include polyvinylpyrrolidone (PVP), for example PVP having a molecular weight of about 2,000 to about 54,000, such as PVP K12, K17, K25 and K30, and surfactants such as phospholipids (e.g., lecithin), cationic surfactants (e.g., myristyl γ-picolinium chloride), anionic surfactants (e.g., sodium lauryl sulfate), etc.

One or more thickening or viscosity adjusting agents can optionally be present, for example cellulosic polymers (e.g., methylcellulose, carboxymethylcellulose, hydroxyethylcellulose, hydroxypropylmethylcellulose), gelatin and gums (e.g., acacia).

One or more preservatives can optionally be present, for example phenol, chlorobutanol, benzyl alcohol, methyl paraben, propyl paraben, benzalkonium chloride and cetylpyridinium chloride.

One or more tonicity adjusting agents can be present, for example sodium chloride, sodium sulfate, dextrose, mannitol and glycerol.

One or more buffering agents can optionally be present, for example buffers derived from acetic, aconitic, citric, glutaric, lactic, malic, succinic, phosphoric and carbonic acids. Typically such a buffer is an alkali or alkaline earth metal salt of such an acid. Phosphate and citrate buffers such as sodium phosphate and sodium citrate are preferred.

In one embodiment the composition comprises a buffering agent and PVP. As disclosed in International Patent Application No. WO 01/87262, incorporated herein by reference, it has been found that PVP can enhance pH control of a composition of the invention, and can strengthen the pH controlling capacity of a conventional buffering agent. For these purposes PVP of relatively low molecular weight, for example about 2,000 to about 11,000, is preferred. PVP K17 is especially preferred, having a molecular weight of about 7,000 to about 11,000. Suitable amounts of PVP are typically about 1 mg/ml to about 100 mg/ml, preferably about 2 to about 50 mg/ml.

Preferably a composition of the invention has a pH of about 3 to about 7. An advantage of the invention is that pH of the composition can often be controlled within a narrower range than hitherto, as a result of reduced oxidative degradation of certain formulation ingredients. For example, in a medroxyprogesterone acetate composition as described herein, pH can typically be controlled within a range of about 3 pH units, e.g., about 4 to about 7, more preferably within a range of about 2.5 pH units, e.g., about 4.5 to about 7, and even more preferably within a range of about 2 pH units, e.g., about 5 to about 7, over a prolonged shelf life.

A composition of the invention can be prepared by a process comprising a first step of formulating a suspension of the drug in particulate form in an aqueous medium that comprises one or more wetting and/or suspending agents, at least one of which is susceptible to oxidative degradation as defined herein. Any suitable formulation method can be used that brings the ingredients of the composition together in a way that results in an aqueous suspension exhibiting controlled flocculation. Such methods are well known in the art. An antioxidant can optionally be added at any suitable point in the formulating step.

Although it is not generally necessary to use an oxygen-depleted atmosphere in the second chamber of the vial, if desired an oxygen-depleted gaseous medium can be provided in a number of ways. An especially convenient way is to prepare the vial, before insertion of the septum or plug, under a blanket of a nonreactive gas such as nitrogen or a noble gas (e.g., argon or helium). An oxygen-depleted gaseous medium preferably consists essentially of nitrogen and oxygen in a weight ratio not less than about 10:1, more preferably not less than about 20:1 and still more preferably not less than about 40:1. Other gases such as carbon dioxide, water vapor and noble gases can be present in such a medium, for example at concentrations in which they occur in ambient air. The gaseous medium can consist essentially of nitrogen.

EXAMPLES

The following examples illustrate aspects of the present invention but are not to be construed as limitations.

Example 1

Samples of commercial Depo-Provera® contraceptive injection product of Pharmacia & Upjohn were prepared according to five treatments described below in a replicated experiment to study effects of headspace conditions on stability of the product. The Depo-Provera® formulation was composed of:

| | |
|---|---:|
| medroxyprogesterone acetate USP sterile, micronized | 150 mg |
| PEG 3350 NF | 28.75 mg |
| polysorbate 80 NF food grade | 2.39 mg |
| sodium chloride USP | 8.64 mg |
| methylparaben NF | 1.36 mg |
| propylparaben NF | 0.148 mg |
| 10% sodium hydroxide solution | q.s. to pH 3.5-7.0 |
| 10% hydrochloric acid solution | q.s. to pH 3.5-7.0 |
| water for injection USP | q.s. to 1 ml |

In a first treatment, herein denoted "as is", the commercial product, a stoppered capped vial of total capacity ~3 ml containing 1.17 ml of the formulation, was used. The headspace contained an atmosphere which was not oxygen-depleted and was essentially ambient air as of the time of filling.

In a second treatment, herein denoted "refreshed", a vial as above was opened to refresh the air in the headspace; the vial was then restoppered, recapped and shaken.

In a third treatment, herein denoted "large", the contents of one commercial product vial were transferred into a rinsed and dried vial of total capacity ~8 ml to provide a large headspace. The vial was stoppered and capped.

In a fourth treatment, herein denoted "small", the contents of three commercial product vials were combined into a single vial of total capacity ~3 ml so that the remaining headspace was very small, no greater than 5% of the total volume of the vial. The vial was restoppered and recapped.

In a fifth treatment, herein denoted "inert", a commercial product vial was opened and the headspace purged with nitrogen for approximately 1 minute before restoppering and recapping.

All samples were inverted and then placed in a Fisher Isotemp® vacuum oven, Model 281 set at 85° C. Samples were removed at selected time points for measurement of pH and polysorbate 80 content. Non-removed samples in the "refreshed" treatment only were opened for about 10 minutes at each time point, then restoppered, recapped and shaken before being returned to the oven. Samples were centrifuged in their vials for 10 minutes at 2,500 rpm to provide a clear supernatant for analysis.

Measurement of pH was by ATI Orion Expandable Ion Analyzer EA 940 with an Orion Microcombination (Catalog no. 9803BN) electrode. Polysorbate 80 was separated by HPLC (HP1090 with Zorbax SB C8, 3.5 µm, 75×4.6 mm column) and fractions of polysorbate 80 containing a fatty acid ester were quantitated by HPLC (HP 1090 with HP Hypersil ODS, 5 mm, 250×4.6 mm column) both in the supernatant (bulk solution) and adsorbed on the drug surface as described below.

Following centrifugation, the supernatant was removed and assayed by HPLC (bulk solution). If traces of solids were present in the supernatant, centrifugation was repeated before assaying. To the remaining deposit in the vial, 1 ml of 10 mg/ml sodium chloride solution was added, followed by vortexing for 10 seconds and shaking for 1 minute. The resulting suspension was centrifuged again for 10 minutes at 2,500 rpm, and the supernatant discarded. Addition of sodium chloride, vortexing, shaking, centrifugation and discarding of supernatant were repeated one more time. Then 0.6 ml of 50% acetonitrile was added to the vial, vortexed to resuspend and shaken for 1 minute, then centrifuged for 10 minutes at 2,500 rpm. The resulting supernatant was carefully transferred to a 2 ml volumetric flask. Addition of acetonitrile, vortexing, shaking, centrifugation and transfer of supernatant were repeated two more times. The material in the volumetric flask was diluted to 2 ml with 50% acetonitrile to provide the solution for polysorbate 80 (adsorbed on drug surface) separation and quantitation by HPLC.

In this example, only the supernatant (i.e., bulk solution) polysorbate content was recorded. An equilibrium exists between polysorbate 80 in bulk solution and adsorbed on the drug, thus bulk solution content is a good indicator of total polysorbate 80 content of the composition.

Data showing effects of headspace condition on pH and polysorbate 80 content are shown in Tables 1 and 2 respectively.

TABLE 1

Effect of headspace condition on pH of Depo-Provera ® samples

| Headspace treatment | days at 85° C. | | | |
|---|---|---|---|---|
| | 0 | 6 | 14 | 49 |
| "as is" | 5.5 | 3.2 | 3.2 | 3.6 |
| "refreshed" | 5.5 | not tested | 3.0 | 3.3 |
| "large" | 5.5 | 2.9 | 2.9 | 3.4 |
| "small" | 5.5 | 3.9 | 3.9 | 4.2 |
| "inert" | 5.5 | 5.4 | 5.2 | 5.0 |

TABLE 2

Effect of headspace condition on polysorbate 80 content (% of theoretical) of Depo-Provera ® samples

| Headspace treatment | days at 85° C. | | | |
|---|---|---|---|---|
| | 0 | 6 | 14 | 49 |
| "as is" | 82 | 42 | 50 | 25 |
| "refreshed" | 82 | not tested | 44 | 7 |
| "large" | 82 | 38 | 39 | none detected |
| "small" | 82 | 81 | 82 | 30 |
| "inert" | 82 | 82 | 81 | 25 |

The "small" and "inert" headspace treatments were representative of the effects of protecting the formulation in the vial from oxidative degradation. The "small" treatment is indicative of conditions in an article of the present invention, wherein the formulation substantially fills the chamber in which it is packaged, with very little headspace.

Up to the 14 days time point, significant oxidative degradation of polysorbate 80 is evident in the data for "as is", "refreshed" and "large" headspace treatments. Polysorbate 80 content declined to 50% or less of theoretical content (Table 2), with a concomitant reduction in pH (Table 1). However, in the "small" and "inert" headspace treatments, no decline in polysorbate 80 content was seen up to 14 days. A moderate reduction in pH occurred in the "small" headspace treatment but not with the "inert" headspace.

By the 49 days time point, degradation of polysorbate 80 was evident in all treatments. An anaerobic degradation mechanism that operates at the high temperature used in this study is believed to be responsible for this late effect. It is believed that real-time aging of product under normal storage conditions over a period of a year or more is simulated by the high temperature accelerated aging of the first 14 days of this study, but that the apparent anaerobic degradation process seen following 49 days of high temperature exposure is not involved to a significant extent in real-time aging.

The data from this study clearly indicate that minimizing exposure of a polysorbate 80 containing formulation to oxygen by substantial elimination of a headspace during storage, as in an article of the present invention, inhibits polysorbate 80 degradation to a very marked and useful degree.

Example 2

Samples of commercial Depo-Provera® contraceptive injection product of Pharmacia & Upjohn from different manufacturing lots were retrieved following up to 5 years storage in conventional single-chamber vials. Settled drug height (SDH) was determined for several vials as an indicator of controlled flocculation properties. SDH is the height of settled drug following shaking of the vial expressed as a percentage of total product height. As controlled flocculation properties are lost, SDH increases, ultimately reaching 100%. A sample showing good controlled flocculation behavior has SDH of about 30%.

When "good" (low SDH) and "bad" (high SDH) samples were compared as to pH, it was found that, within any one lot, pH was always lower in the "bad" than in the "good" samples. However, there was no clear correlation of pH with SDH across different lots, suggesting that increase in SDH is not caused by pH per se but that relative lowering of pH within a lot is merely an indicator of a degradative change causing the SDH increase.

Polysorbate 80 contents in bulk solution and adsorbed to the drug surface were measured, by the procedure described in Example 1, for "good" and "bad" samples within several lots. The "bad" samples were generally found to have lower amounts of polysorbate 80 remaining, both in bulk solution and adsorbed to the drug surface, than the "good" samples from the same lot, as shown in Table 3.

It is contemplated that substantial elimination of headspace will minimize loss of polysorbate 80 during storage (as demonstrated in Example 1) and will thereby permit longer maintenance of controlled flocculation behavior.

TABLE 3

Comparison of "good" and "bad" samples of aged Depo-Provera ® product from the same manufacturing lot

| Lot | Sample | pH | polysorbate 80 (% of theoretical) | |
|---|---|---|---|---|
| | | | bulk solution | adsorbed on drug |
| 1 | "good" | 3.90 | 3.5 | 14.0 |
| | "bad" | 3.71 | 1.2 | 13.8 |
| 2 | "good" | 3.68 | 1.3 | 13.5 |
| | "bad" | 3.46 | 1.1 | 13.3 |
| 3 | "good" | 3.93 | 0.9 | 13.8 |
| | "bad" | 3.64 | 0.3 | 11.1 |
| 4 | "good" | 3.97 | 2.4 | 13.2 |
| | "bad" | 3.72 | 0.4 | 10.0 |
| 5 | "good" | 4.09 | 4.2 | 15.8 |
| | "bad" | 3.82 | 3.4 | 13.5 |
| 6 | "good" | 4.12 | 2.3 | not tested |
| | "bad" | 3.92 | 0.7 | not tested |
| 7 | "good" | 3.49 | 1.5 | 17.7 |
| | "bad" | 3.19 | 1.4 | 15.7 |

Example 3

An antioxidant or a chelating agent was added to samples of commercial Depo-Provera® formulation to study effects of these agents on stability of the product. The antioxidant used was Trolox®, 6-hydroxy-2,5,7,8-tetramethylchroman-2-carboxylic acid 97% (Aldrich), and the chelating agent used was DTPA pentasodium salt 40% in water (J. T. Baker), diluted with water to 100 mg DTPA/ml.

Under constant stirring, bulk Depo-Provera suspension was pipetted in an amount of 1.1 ml into each of 14 vials. Into each of 4 of these vials ("set 2") had previously been placed 1 mg of Trolox. Into each of another 4 vials ("set 3"), after addition of the suspension, was added 10 µl of diluted DTPA. Contents of all vials containing Depo-Provera plus Trolox or DTPA, and of 4 additional vials ("set 1") containing only Depo-Provera, were adjusted to a pH of 6.3 to 6.9 with 0.2N hydrochloric acid or 12.5 mg/ml sodium hydroxide solution. The remaining 2 vials containing only Depo-Provera did not have their contents pH-adjusted. These are denoted the "control 0" vials. Half of each of the "set 1", "set 2", "set 3" and "control 0" vials were fitted with Helvoet stoppers and capped, and the remaining half were fitted with Dalkyo stoppers and capped. The "control 0" vials were placed in a freezer. The other vials were placed in a Fisher Isotemp® vacuum oven, Model 281, set at 85° C. Samples were removed from the oven or freezer after 10 days and resuspended by shaking prior to measurement of pH and bulk solution polysorbate 80 content by the procedures described in Example 1.

Data showing effects of antioxidant (Trolox) and chelating agent (DTPA) on pH and polysorbate 80 content are shown in Table 4.

TABLE 4

Effects of antioxidant and chelating agent on Depo-Provera ® samples

| treatment | additive | stopper | pH initial | pH final | polysorbate 80 (% of theoretical) |
|---|---|---|---|---|---|
| control 0 | | | 4.0 | 4.1 | 92 |
| set 1 | | Helvoet | 6.6 | 3.3 | 57 |
| set 2 | Trolox | Helvoet | 6.7 | 3.7 | 82 |
| set 3 | DTPA | Helvoet | 6.3 | 6.2 | 78 |
| set 1 | | Daikyo | 6.6 | 2.7 | 66 |
| set 2 | Trolox | Daikyo | 6.8 | 3.2 | 82 |
| set 3 | DTPA | Daikyo | 6.7 | 5.7 | 79 |

Both the antioxidant and the chelating agent significantly reduced polysorbate 80 degradation in this study.

Example 4

A parenteral aqueous suspension formulation of medroxyprogesterone acetate having the following composition is prepared and packaged in the upper chamber of an Act-O-Vial® mixing vial, substantially filling the upper chamber:

| | |
|---|---|
| medroxyprogesterone acetate | 150 mg |
| PEG 3350 | 30 mg |
| polysorbate 80 | 2.5 mg |
| sodium chloride | 9 mg |
| methylparaben | 1.5 mg |
| propylparaben | 0.15 mg |
| water for injection | q.s. to 1 ml |

The lower chamber of the Act-O-Vial is air-filled. The above formulation is especially suitable for intramuscular injection.

Example 5

A parenteral aqueous suspension formulation of medroxyprogesterone acetate having the following composition is prepared and packaged in the upper chamber of an Act-O-Vial® mixing vial, substantially filling the upper chamber:

| | |
|---|---|
| medroxyprogesterone acetate | 104 mg |
| PEG 3350 | 18.7 mg |
| polysorbate 80 | 1.95 mg |
| sodium chloride | 5.2 mg |
| methylparaben | 1.04 mg |
| propylparaben | 0.10 mg |
| monobasic sodium phosphate monohydrate | 0.45 mg |
| dibasic sodium phosphate dodecahydrate | 0.38 mg |
| L-methionine | 0.98 mg |
| PVP K17 PF | 3.25 mg |
| sodium hydroxide | q.s. to pH 3.5-7.0 |
| hydrochloric acid | q.s. to pH 3.5-7.0 |
| water for injection | q.s. to 0.65 ml |

The lower chamber of the Act-O-Vial is air-filled. The above formulation is especially suitable for subcutaneous injection.

What is claimed is:

1. An article of manufacture comprising a vial having
   (a) a first chamber that is substantially filled with a parenterally deliverable aqueous suspension that comprises (i) an aqueous medium; (ii) a drug in solid particulate form in a therapeutically effective amount suspended in the medium; and (iii) one or more wetting and/or suspending agents in an amount effective to provide controlled flocculation of the drug, at least one ingredient of the formulation being susceptible to oxidative degradation;
   (b) a second chamber that is substantially empty but for a gaseous medium;
   (c) a septum separating the first and second chambers and impermeable to the gaseous medium; and
   (d) actuating means effective to bring the aqueous suspension and the gaseous medium into contact by breach of the septum such that the gaseous medium acts as an effective headspace for agitation of the formulation.

2. The article of claim 1 wherein the second chamber forms a lower compartment and the first chamber forms an upper compartment; said lower and upper compartments being separated by a constriction wherein the septum in a form of a substantially airtight and watertight plug is engaged; said upper compartment having an annular neck terminating in an open end; said neck having engaged thereon a closure structure comprising (i) a resiliently flexible stopper having a lower sealing portion seated within the neck and an upper protruding portion that projects coaxially beyond the of the neck; said stopper having a deep recess open at the base thereof and closed at the apex thereof such that the apex of the recess is in proximity to the upper surface of the protruding portion, defining a thin wall portion of the stopper that permits a sharp tip of a syringe needle to be inserted through the thin wall into the upper compartment for withdrawal of the formulation therein; and (ii) a cap assembly that incorporates said actuating means, wherein said actuating means is a means for applying hydraulic pressure via the formulation in the upper compartment to the plug, said pressure tending to disengage the plug from the constriction, thereby pushing the plug into the lower compartment to bring the formulation into contact with the gaseous medium in the lower compartment.

3. The article of claim 2 wherein the means for applying hydraulic pressure comprises a sleeve of the cap assembly that is snugly disposed around and slidingly engaged with the protruding portion of the stopper; and wherein the sealing portion of the stopper is of larger diameter than the protruding portion and defines at the interface therewith an annular shoulder; said sleeve, adjacent to a lower end thereof, being fracturably connected to an annular gripping portion of the cap assembly; said gripping portion surrounding an radially outward projecting rim formed at the open end of the neck and having at the lower edge of the gripping portion a plurality of substantially uniformly spaced projections extending radially inward; said gripping portion comprising an annular plate that overlies the open end of the neck and circumscribes a plate opening of diameter smaller than the neck opening, such that the annular plate projects radially inward to overlap the stopper shoulder and thereby positively retain the stopper in the neck; said sleeve having, on an outer surface thereof, a plurality of parallel and substantially uniformly spaced ramps that extend axially from and converge with the sleeve toward the gripping portion and that function as a locking means for retaining the sleeve in an actuated position; said sleeve being actuatable by depression thereof to break the fracturable connection and engage with the stopper shoulder to push the stopper downward, thereby creating hydraulic pressure in the upper compartment.

4. The article of claim 1 wherein the gaseous medium is air.

5. The article of claim 1 wherein the at least one oxidative degradation susceptible ingredient present in the formulation comprises a polyoxyethylene chain.

6. The article of claim 1 wherein the at least one oxidative degradation susceptible ingredient present in the formulation is a polyoxyethylene surfactant.

7. The article of claim 6 wherein the polyoxyethylene surfactant is a polysorbate.

8. The article of claim 6 wherein the polyoxyethylene surfactant is polysorbate 80.

9. The article of claim 8 wherein the polysorbate 80 is present in an amount of about 0.1 to about 10 mg/ml.

10. The article of claim 8 wherein the polysorbate 80 is present in an amount of about 1 to about 5 mg/ml.

11. The article of claim 1 wherein the drug present in the formulation is of low water solubility.

12. The article of claim 1 wherein the drug present in the formulation is selected from the group consisting of acetohexamide, acetylsalicylic acid, alclofenac, allopurinol, atropine, benzthiazide, carprofen, celecoxib, chlordiazepoxide, chlorpromazine, clonidine, codeine, codeine phosphate, codeine sulfate, deracoxib, diacerein, diclofenac, diltiazem, eplerenone, estradiol, etodolac, etoposide, etoricoxib, fenbufen, fenclofenac, fenprofen, fentiazac, flurbiprofen, griseofulvin, haloperidol, ibuprofen, indomethacin, indoprofen, ketoprofen, lorazepam, medroxyprogesterone acetate, megestrol, methoxsalen, methylprednisone, morphine, morphine sulfate, naproxen, nicergoline, nifedipine, niflumic, oxaprozin, oxazepam, oxyphenbutazone, paclitaxel, phenindione, phenobarbital, piroxicam, pirprofen, prednisolone, prednisone, procaine, progesterone, pyrimethamine, rofecoxib, sulfadiazine, sulfamerazine, sulfisoxazole, sulindac, suprofen, temazepam, tiaprofenic acid, tilomisole, tolmetic and valdecoxib.

13. The article of claim 1 wherein the drug present in the formulation is a steroidal drug.

14. The article of claim 13 wherein the steroidal drug is selected from the group consisting of clostebol, estradiol, exemestane, medroxyprogesterone, methylprednisolone, testosterone and pharmaceutically acceptable esters and salts thereof.

15. The article of claim 13 wherein the steroidal drug is selected from the group consisting of estradiol cypionate, exemestane and medroxyprogesterone acetate.

16. The article of claim 13 wherein the steroidal drug is medroxyprogesterone acetate.

17. The article of claim 16 wherein the medroxyprogesterone acetate is present in an amount of about 10 to about 400 mg/ml.

18. The article of claim 16 wherein the medroxyprogesterone acetate is present in an amount of about 30 to about 300 mg/ml.

19. The article of claim 16 wherein the medroxyprogesterone acetate is present in an amount of about 50 to about 200 mg/ml.

20. The article of claim 16 wherein the formulation comprises:
(a) medroxyprogesterone acetate, 100-200 mg/ml;
(b) polyethylene glycol of molecular weight 3000-4000, 20-40 mg/ml;
(c) polysorbate 80, 2-4 mg/ml;
(d) sodium chloride, 6-12 mg/ml; and
(e) optionally at least one parenterally acceptable preservative, 0.1-5 mg/ml total.

21. The article of claim 16 wherein the formulation comprises:
(a) medroxyprogesterone acetate, about 150 mg/ml;
(b) polyethylene glycol of molecular weight about 3350, about 30 mg/ml;
(c) polysorbate 80, about 2.5 mg/ml;
(d) sodium chloride, about 9 mg/ml;
(e) methylparaben, about 1.5 mg/ml;
(f) propylparaben, about 0.15 mg/ml; and
(g) water for injection, q.s.

22. The article of claim 16 wherein the formulation comprises, in a volume of about 0.65 ml:
(a) medroxyprogesterone acetate, about 104 mg;
(b) polyethylene glycol of molecular weight about 3350, about 18.7 mg;
(c) polysorbate 80, about 1.95 mg;
(d) sodium chloride, about 5.2 mg;
(e) methylparaben, about 1.04 mg;
(f) propylparaben, about 0.10 mg;
(g) monobasic sodium phosphate monohydrate, about 0.45 mg;
(h) dibasic sodium phosphate dodecahydrate, about 0.38 mg;
(i) L-methionine, about 0.98 mg;
(j) polyvinylpyrrolidone K17, about 3.25 mg; and
(k) water for injection, q.s.

* * * * *